(12) United States Patent
Hiramoto et al.

(10) Patent No.: US 7,081,368 B2
(45) Date of Patent: Jul. 25, 2006

(54) METHOD FOR DETECTING GAS WITH THE USE OF PHOTOCURRENT AMPLIFICATION AND THE LIKE AND GAS SENSOR

(75) Inventors: Masahiro Hiramoto, Takatsuki (JP); Masaaki Yokoyama, Nishinomiya (JP); Manabu Yoshida, Suita (JP)

(73) Assignee: Japan Science and Technology Corporation, Kawaguchi (JP)

( * ) Notice: Subject to any disclaimer, the term of this patent is extended or adjusted under 35 U.S.C. 154(b) by 682 days.

(21) Appl. No.: 10/362,907

(22) PCT Filed: Aug. 13, 2001

(86) PCT No.: PCT/JP01/06996

§ 371 (c)(1),
(2), (4) Date: Feb. 27, 2003

(87) PCT Pub. No.: WO02/21114

PCT Pub. Date: Mar. 14, 2002

(65) Prior Publication Data

US 2003/0182986 A1 Oct. 2, 2003

(30) Foreign Application Priority Data

Sep. 1, 2000 (JP) .............................. 2000-265226

(51) Int. Cl.
*H01L 21/66* (2006.01)

(52) U.S. Cl. ........................... 438/14; 438/17; 438/18; 438/49; 257/440

(58) Field of Classification Search ................. 438/14, 438/17, 18, 49, 82, 88, 93; 257/440; 73/31.06, 73/335.02, 335.05

See application file for complete search history.

(56) References Cited

U.S. PATENT DOCUMENTS 4,836,012 A 6/1989 Doty et al. ................... 73/23

(Continued)

FOREIGN PATENT DOCUMENTS

GB 1429848 3/1976

(Continued)

OTHER PUBLICATIONS

R. Brina et al.; "Chemiresistor Gas Sensors Based on Photoconductivity Changes in Phthalocyanine Thin Films: Enhancement of Response toward Ammonia by Photo-electrochemical Deposition with Metal Modifiers"; *Analytical Chemistry*; 1990, vol. 62, pp. 2357-2365./Cited in the International Search Report.

(Continued)

*Primary Examiner*—Kevin M. Plcardat
(74) *Attorney, Agent, or Firm*—Armstrong, Kratz, Quintos, Hanson & Broooks, LLP (57) ABSTRACT

An indium electrode film (2) is formed closely adhering to one face of an organic semiconductor film (1) made of copper phthalocyanine while a gold electrode film (3) is formed on the other face. A voltage is applied to the organic semiconductor film (1) so that the indium electrode (2) side is biased positively. By applying a voltage so that the electrode (2) side is charged positively and irradiating with a light having a wavelength absorbable by the organic semiconductor film (1) the phenomenon of photocurrent multiplication arises at the interface of the organic semiconductor film (1) and the electrode (2). When put under an oxygen or moisture atmosphere in the above state, this gas sensor can detect oxygen or moisture depending on a change in photocurrent due to the multiplication.

15 Claims, 8 Drawing Sheets

U.S. PATENT DOCUMENTS

| | | | |
|---|---|---|---|
| 4,900,817 A | | 2/1990 | Batzel et al. ............... 540/128 |
| 5,215,643 A | * | 6/1993 | Kusanagi et al. ........... 204/412 |
| 5,936,250 A | * | 8/1999 | Baliga et al. ............... 250/373 |
| 6,269,680 B1 | * | 8/2001 | Prieve et al. .............. 73/23.21 |
| 6,290,388 B1 | * | 9/2001 | Saul et al. .................. 257/470 |
| 6,777,024 B1 | * | 8/2004 | Hattori et al. ................ 427/58 |

FOREIGN PATENT DOCUMENTS

| | | |
|---|---|---|
| JP | 62-076576 | 4/1987 |
| JP | 5-80008 | 3/1993 |
| JP | 6-313759 | 11/1994 |

OTHER PUBLICATIONS

M. Hiramoto et al.; "Photoinduced Hole Injection Multiplication in p-Type Quinacridone Pigment Films"; *Japanese Journal of Applied Physics, part 2*; Letters, 1996, vol. 35, pp. 349-351/Cited in the International Search Report./Discussed in the specification.

J. W. Couves et al.; "Effect of Oxidising Atmosphere on the Conductivity and Photoconductivity of Cofacial Metallophthalocyanine Polymers"; *Synthetic Metals*; 1989, vol. 29, pp. 77-82./Cited in the International Search Report.

R.A. Collins et al., "Electrical, Structural and Gas Sensing Properties of Zinc Phthalocyanine Thin Films"; *Thin Solid Films*; 1986, vol. 145, pp. 133-145./Cited in the International Search Report.

A. Krier et al.; "The Influence of $NO_2$ on the Conductivity of Chloro-Aluminum Phthalocyanin e Thin Films"; *Journal of Physics and Chemistry of Solids*; 1997, vol. 58, pp. 711-716./Cited in the International Search Report.

Tomozawa et al; "Metal-Polymer Schottky Barriers on Processible Polymers"; XP002317819; Synthetic Metals 28 (1989) pp. C687-I90.

Supplemental European Search Report dated Mar. 1, 2005.

* cited by examiner

Im-PTC

DQ t-BuPh-PTC

MEROCYANINE

PhEt-PTC

PORPHYRIN SKELETON

Me-PTC

MPc

NTCDA

POLYCARBONATE

POLYVINYL BUTYRAL

POLYVINYL CARBOZOLE

POLYMETHYL PHENYLSILANE

METHOD FOR DETECTING GAS WITH THE USE OF PHOTOCURRENT AMPLIFICATION AND THE LIKE AND GAS SENSOR

TECHNICAL FIELD

The present invention relates to a method for sensing atmospheric gas using a cell having an organic semiconductor film, and to a gas sensor implementing this method.

BACKGROUND ART

Conventionally, as a gas sensor using an organic semiconductor, semiconductor gas sensors of the electric resistance type wherein comb like electrodes are formed on the surface of an organic semiconductor film and gas concentration is sensed using the fact that the dark conductivity of the organic semiconductor layer changes due to adsorption of gas have been generally used. As an example of such a gas sensor, $NO_2$ sensors using a change in dark conductivity of a phthalocyanine-based thin film are known (See M. Passard, A. Pauly, J. P. Germain, C. Maleysson, Synthetic Metals, 80, 25 (1996), for example.)

On the other hand, the present invention is based on the photocurrent multiplication phenomenon occurring at an organic/metallic interface (See M. Hiramoto, T. Imahigashi, M. Yokoyama, Applied Physics Letters, 64, 187 (1994), for example, with regard to an n-type organic semiconductor, and M. Hiramoto, S. Kawase, M. Yokoyama, Jpn, J. Appl. Phys., 35, L349 (1996), for example, with regard to a p-type organic semiconductor.)

In the conventional gas sensor using an organic semiconductor as described above, change in dark conductivity due to adsorbed gas is used for sensing the adsorbed gas. However, since the dark conductivity of the organic semiconductor is extremely small, and the current is measured by means of comb like electrodes of which electrode-to-electrode distance is normally about 100 μm, an absolute value of the detected current is very small in the order of nA (nano ampere), leading the drawback that it is difficult to achieve accurate measurement.

In addition, since the change in dark conductivity is measured by measuring a change in resistance of entire organic thin film bulk, diffusion of molecules into the film bulk is a rate-determining factor, so that the drawback of slow response also arises.

In view of the above, it is an object of the present invention to provide a gas sensing method which improves the sensitivity of gas sensing and the response speed, and a gas sensor for implementing the method.

DISCLOSURE OF INVENTION

A current multiplication gas sensor according to the present invention uses a sandwich cell formed by sandwiching an organic semiconductor layer between two metallic electrodes and senses a gas by measuring a change in photo current associated with photocurrent multiplication at an organic/metallic interface flowing in the cell under voltage application or a change in dark current which occurs when not irradiated with light.

The first method of the present invention that uses a change in photocurrent is a gas sensing method for sensing a gas to be sensed using a sandwich cell formed by sandwiching a photoconductive organic semiconductor layer between two metallic electrodes, the method comprising the steps as follows:

(A) a step of irradiating the organic semiconductor layer with light in the condition that a voltage is applied on the organic semiconductor layer by the electrodes, thereby causing a multiplied photocurrent to generate at an organic/metallic interface;

(B) a step of bringing the gas to be sensed into contact with the organic/metallic interface where photocurrent multiplication is occurring, in the condition of (A); and (C) a step of measuring a photocurrent flowing in the organic semiconductor layer to sense gas on the basis of a change in photocurrent associated with the contact of the gas to be sensed.

The second method of the present invention that uses a change in dark current when irradiation with light is not executed is a gas sensing method for sensing a gas to be sensed using a sandwich cell formed by sandwiching an organic semiconductor layer between two metallic electrodes, the method comprising the steps as follows:

(A) a step of applying a voltage to the organic semiconductor layer by the electrodes to cause occurrence of a multiplied dark current at an organic/metallic interface;

(B) a step of bringing the gas to be sensed into contact with the organic/metallic interface where multiplication of dark current is occurring; and (C) a step of measuring a dark current flowing in the organic semiconductor layer to sense gas on the basis of a change in dark current associated with the contact of the gas to be sensed.

According to the present invention, since a change in injection current associated with photocurrent multiplication or dark current multiplication at the organic/metallic interface is used for sensing a gas, the absolute value of the detected current is larger than the case of the conventional gas sensor which measures a change in dark conductivity of organic semiconductor, so that the sensitivity is improved and the response speed increases because of the change in injection current at the interface.

A photocurrent multiplication gas sensor for implementing the first method of the present invention that uses a change in photo current comprises: a sandwich cell formed by sandwiching a photoconductive organic semiconductor layer between two metallic electrodes; a power supply for applying a voltage to the organic semiconductor layer by the electrodes; an optical system for irradiating the organic semiconductor layer with light; an opening for bringing a gas to be sensed into contact with an organic/metallic interface where photocurrent multiplication occurs due to voltage application by the power supply and light irradiation by the optical system; and a current measuring circuit for measuring a photocurrent flowing in the organic semiconductor layer, thereby sensing a gas on the basis of a change in photocurrent associated with the contact of the gas to be sensed.

Figure 2:
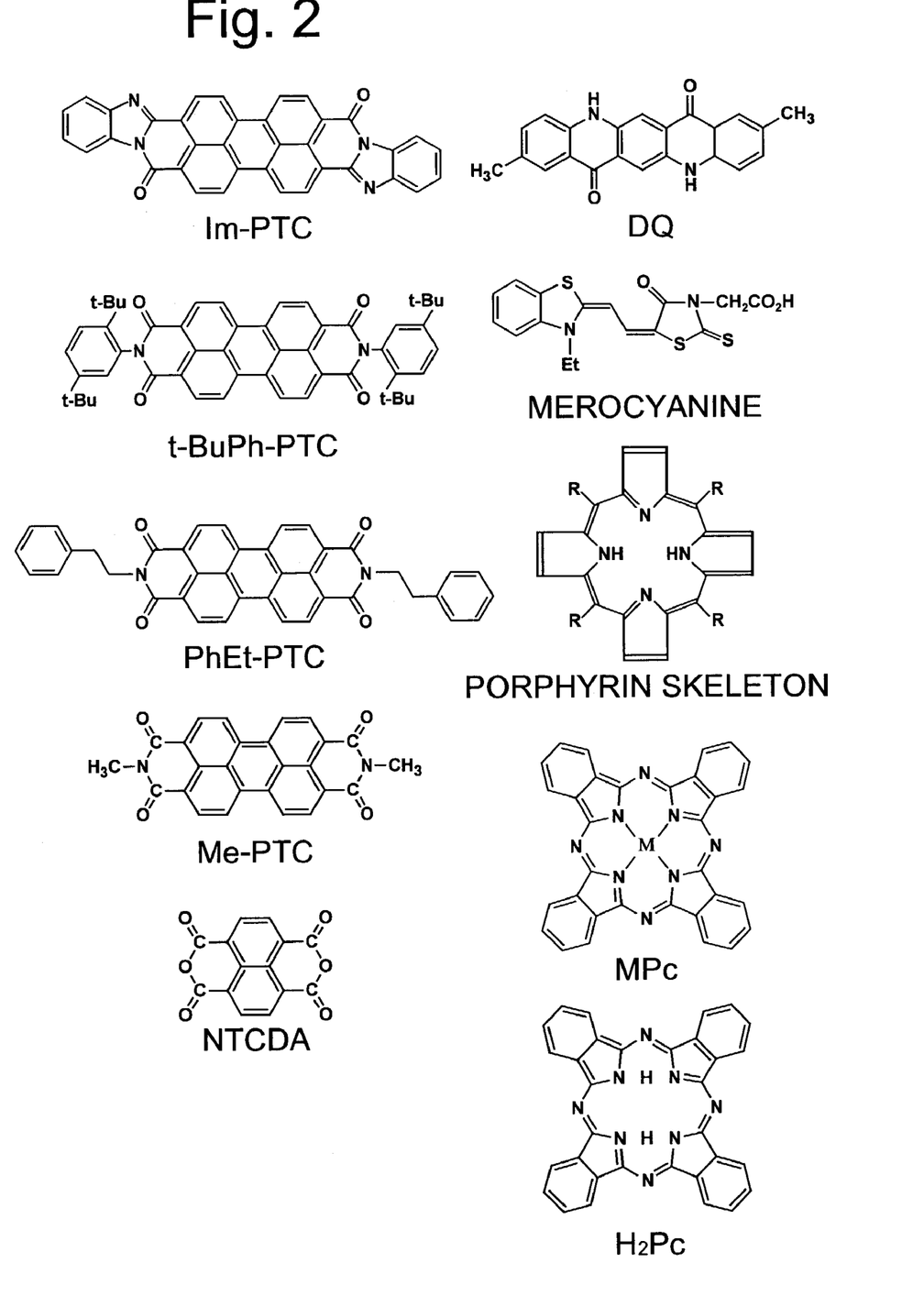
FIG. 2 shows chemical formulae representing some examples for organic semiconductor used in the present invention.

Organic semiconductors can be classified into p-type and n-type semiconductors, and the gas sensor of the present invention can be realized by either type of semiconductor. Examples of such organic semiconductor are shown in FIG. 2. Of course, organic semiconductors that can be used in the present invention are not limited to these examples.

When the organic semiconductor layer is a p-type organic semiconductor layer, by applying a voltage so that the metallic electrode of the organic/metallic interface where photocurrent multiplication should occur is biased to the plus voltage side, it is possible to sense oxygen or moisture from an increase in the photocurrent When the organic semiconductor layer is a p-type organic semiconductor layer, it is preferred that the metallic electrode of the organic/metallic interface where photocurrent multiplication should occur is formed of a metal having a small work function. As one example of such metal, indium can be recited.

Examples of p-type organic semiconductor include phthalocyanine pigments and derivatives thereof (MPc having various metals in the center, $H_2Pc$ not having a metal, those having various surrounding substituents), quinacridone pigment (DQ), porphyrin, merocyanine and the like and derivatives thereof.

When the organic semiconductor layer is an n-type organic semiconductor layer, a voltage is applied so that the metallic electrode of the organic/metallic interface where photocurrent multiplication should occur is biased to the minus voltage side.

Examples of the n-type organic semiconductor include perylene pigments and derivatives (a variety of derivatives having different substituents bonded to the nitrogen atom are known, such as t-BuPh-PTC, PhEt-PTC and the like, or Im-PTC having high photocurrent converting ability), naphthalene derivatives (perylene pigments in which perylene skeleton is replaced by naphthalene, for example, NTCDA), C60 and so on.

When perylene-based pigments or naphthalene derivatives are used as the n-type organic semiconductor, it is possible to sense oxygen from a decrease in photocurrent thereof.

Also when naphthalene derivatives are used as the n-type organic semiconductor, it is possible to sense moisture from a decrease in photocurrent thereof.

In the gas sensor using the n-type organic semiconductor, it is preferred that the metallic electrode of the organic/metallic interface where photocurrent multiplication should occur is formed of a metal having a large work function.

It is preferred that the voltage applied by the power supply is set so as to cause a current change of larger number of electrons than the number of adsorbed gas molecules.

A current multiplication gas sensor for implementing the second method of the present invention using change in dark current in the absence of light irradiation comprises: a sandwich cell formed by sandwiching an organic semiconductor layer between two metallic electrodes; a power supply for applying a voltage to the organic semiconductor layer by the electrodes; an opening for bringing a gas to be sensed into contact with an organic/metallic interface where current multiplication occurs due to voltage application by the power; and a current measuring circuit for measuring a dark current flowing in the organic semiconductor layer, thereby sensing a gas on the basis of a change in dark current associated with the contact of the gas to be sensed.

As the organic semiconductor used in the current multiplication gas sensor using change in dark current, any of the aforementioned organic semiconductors can be used.

The first form of the organic semiconductor layer is an evaporated film of organic semiconductor.

Figure 3:
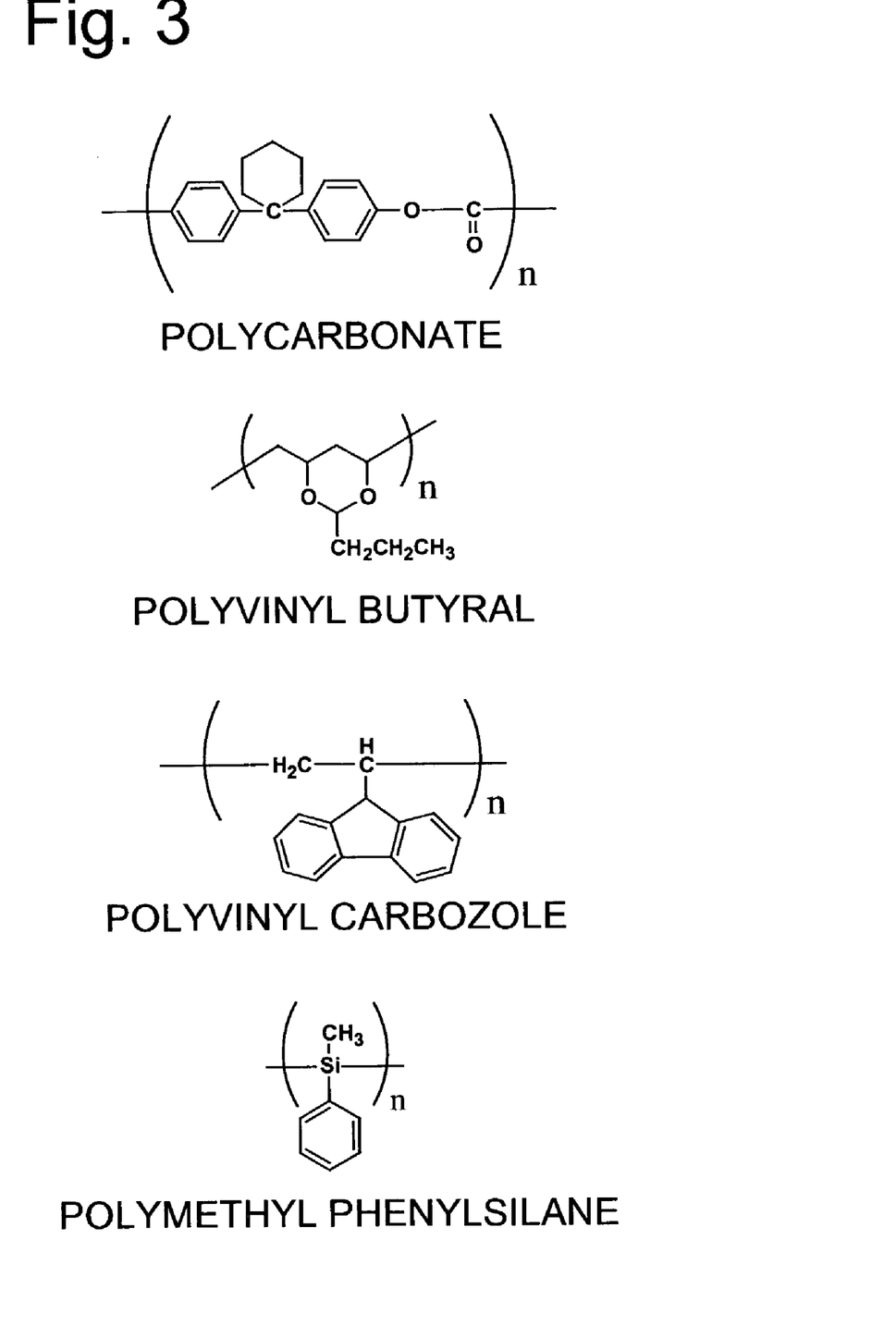
FIG. 3 shows chemical formulae representing some examples for resin used in the present invention for dispersing an organic semiconductor when an organic semiconductor layer is implemented by a resin-dispersed organic semiconductor film.

The second form of the organic semiconductor layer is a resin-dispersed organic semiconductor film wherein an organic semiconductor is dispersed in a resin. Examples of the resin into which the organic semiconductor is dispersed include general-purpose polymers such as polycarbonate, polyvinyl butyral, polyvinyl alcohol, polystyrene and polymethyl methacrylate, conductive polymers such as polyvinyl carbazole, polymethyl phenylsilane and polydimethyl silane, and so on. Chemical formulae of some of these resins are shown in FIG. 3.

The resin-dispersed organic semiconductor film can be formed by applying a mixture of the organic semiconductor and the resin in a solvent on an electrode substrate by way of a spin coat method or a bar coat method (method of extending a dispersion applied on the substrate using a metallic bar with a groove) for forming a film.

According to the present invention, using the sandwich cell formed by sandwiching an organic semiconductor between two metallic electrodes, a change in injection current associated with photocurrent multiplication or dark current multiplication at the organic/metallic interface is used for sensing gas, so that the absolute value of the sensed current becomes large and hence the sensitivity is improved. In addition, since a change in injection current is detected at the interface, the response speed can be improved.

BEST MODE FOR CARRYING OUT THE INVENTION

Next, the present invention will be explained in detail with reference to the drawings.

FIRST EMBODIMENT

The first embodiment will be described by way of an example where a p-type organic semiconductor is used.

Figure 1:
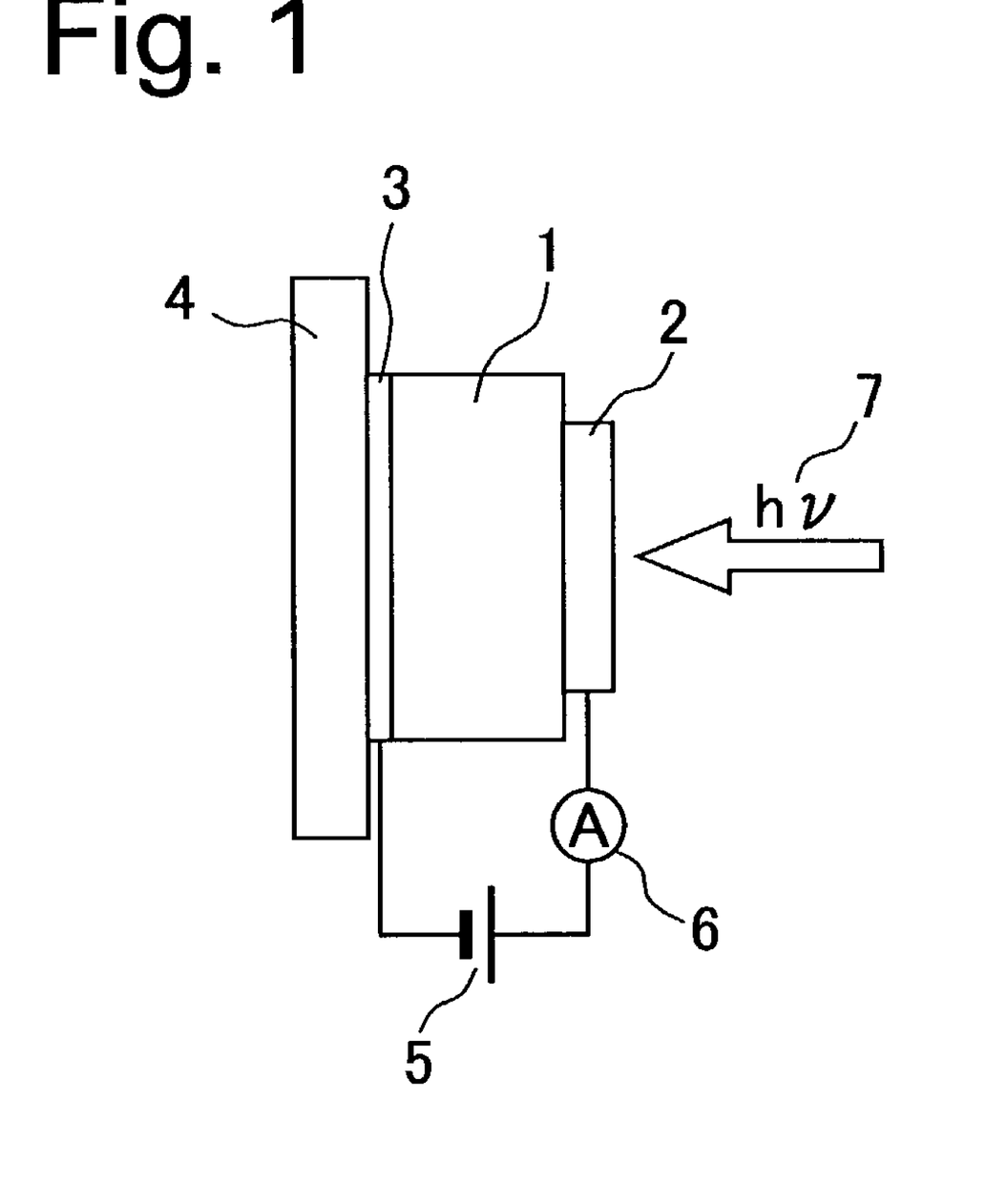
FIG. 1 is a section view showing a structure of one embodiment of a photocurrent multiplication gas sensor device of the present invention.

FIG. 1 is a schematic configuration view of a gas sensor device in which a section view of a sandwich cell structure of a photocurrent multiplication gas sensor device according to the first embodiment is shown together with an electric circuit. The reference numeral 1 denotes an organic semiconductor thin film which is a copper phthalocyanine (CuPc: the center metal M is Cu in the chemical formula represented as MPc in FIG. 2) evaporated film having a film thickness of about 1,000 nm. The reference numeral 2 denotes a metallic electrode thin film which is formed on one surface of the organic semiconductor film 1 so as to closely contact with the same, which is an In (indium) evaporated film having a film thickness of about 100 nm. The reference numeral 3 denotes another metallic electrode thin film which is an Au (gold) evaporated film having a film thickness of about 40 nm and formed on the surface of the organic semiconductor thin film 1, which is opposite to the surface on which the In electrode 2 is formed. The side of the organic semiconductor thin film 1 on which the In electrode 2 is formed is irradiated with light so that the gas to be sensed comes into contact therewith. The reference numeral 4 denotes a glass substrate which supports the present gas sensor device via the Au electrode 3. The reference numeral 5 denotes a power source for applying a voltage on the present device and connected between the electrode thin films 2 and 3 so that the In electrode 2 side is biased toward the plus voltage side. The reference numeral 6 denotes an ampere meter for monitoring the current flowing in the present device, which is connected between the power source 5 and the In electrode 2. The reference numeral 7 denotes monochromatic light with which the organic semiconductor thin film 1 of the present device is irradiated from the In electrode 2 side.

The present device can be formed according to the evaporation method, by evaporating the Au electrode thin film 3 on the glass substrate 4, evaporating the copper phthalocyanine thin film 1 thereon, and evaporating the In electrode thin film 2 thereon.

When the present gas sensor is irradiated with light having a wavelength of 570 nm as the monochromatic light that can be absorbed by the organic semiconductor thin film 1, while applying a voltage on the gas sensor so that the In electrode 2 is positive with respect to the Au electrode 3, the photocurrent multiplication phenomenon occurs at the CuPc/In interface by the mechanism as will be described later.

Then as the gas sensor is operated under a variety of gas atmospheres, the photocurrent due to multiplication changes depending on the gas concentration, and this change in photocurrent is detected by the ampere meter 6.

Next, effects of the present invention will be described by way of concrete examples.

Figure 4:
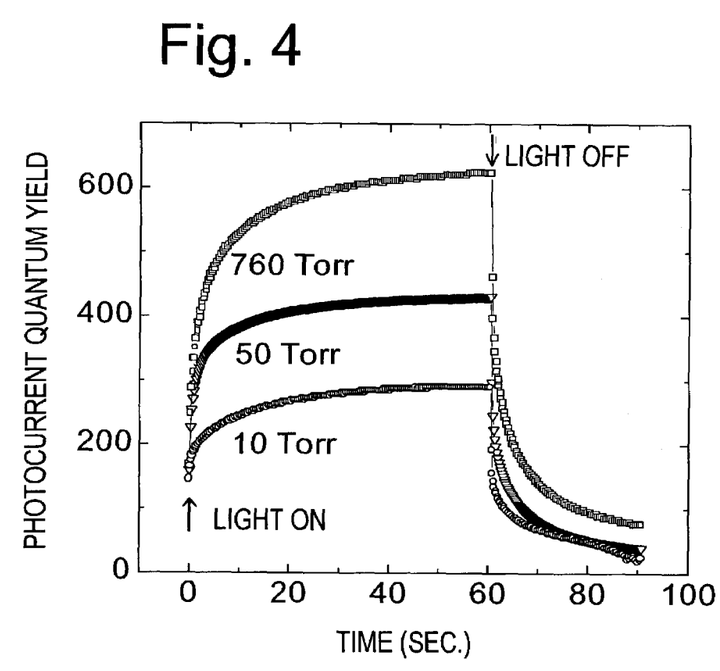
FIG. 4 is a graph showing photo response characteristics of one embodiment under various oxygen pressures.

FIG. 4 shows photo response of the device under a variety of oxygen pressures, the oxygen being introduced after applying a voltage of 10V on the device of FIG. 1 and evacuating by a rotary pump. The horizontal axis represents time and the vertical axis represents photocurrent quantum yield (multiplication factor) which is calculated by dividing the number of carries flowing in the device as photocurrent by the number of photons that the organic semiconductor thin film 1 has actually absorbed. For example, "quantum yield of 600" means that 600 carriers flow through the device by one photon. This is called a photocurrent multiplication phenomenon. The photocurrent multiplication phenomenon in the organic semiconductor thin film 1 formed of CuPc is first observed by the inventors of the present invention.

Figure 5:
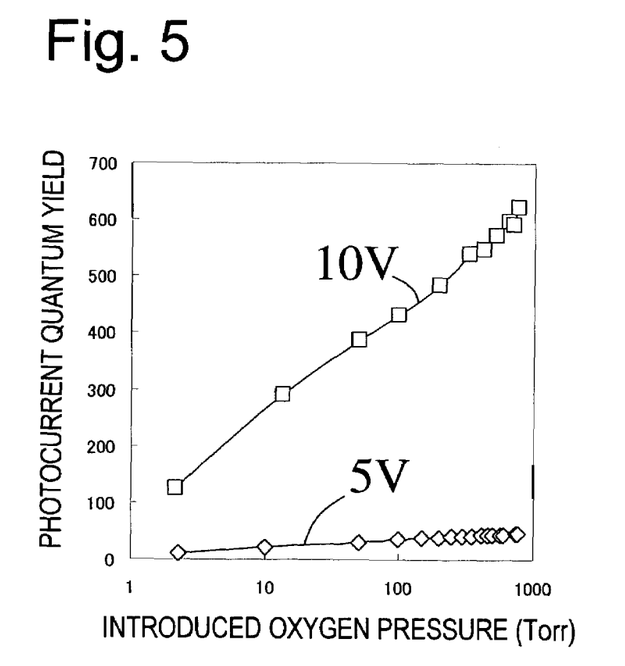
FIG. 5 is a graph showing dependence of photocurrent quantum yield on oxygen pressure in the same embodiment.

FIG. 5 plots the photocurrent quantum yield measured in the manner as described above in relative to the introduced oxygen pressure. From FIGS. 4 and 5, it can be realized that the multiplication factor increases quantitatively as the oxygen pressure increases, and since the response is reversible, it is possible to use this characteristic for sensing oxygen. The larger the applied voltage, the larger the change due to oxygen introduction becomes large so that the sensitivity increase At the applied voltage of 10V, the amount of increase in photocurrent with respect to the change in oxygen pressure from 1 Torr to 760 Torr reached to as high as about 0.5 mA/cm$^2$. Such a large change in current amount that reaches to milli ampere per 1 cm$^2$ as described above cannot be realized when the change in resistance is measured by comb like electrodes. Also it is expected that this value will become larger if a larger voltage is applied.

Figure 6:
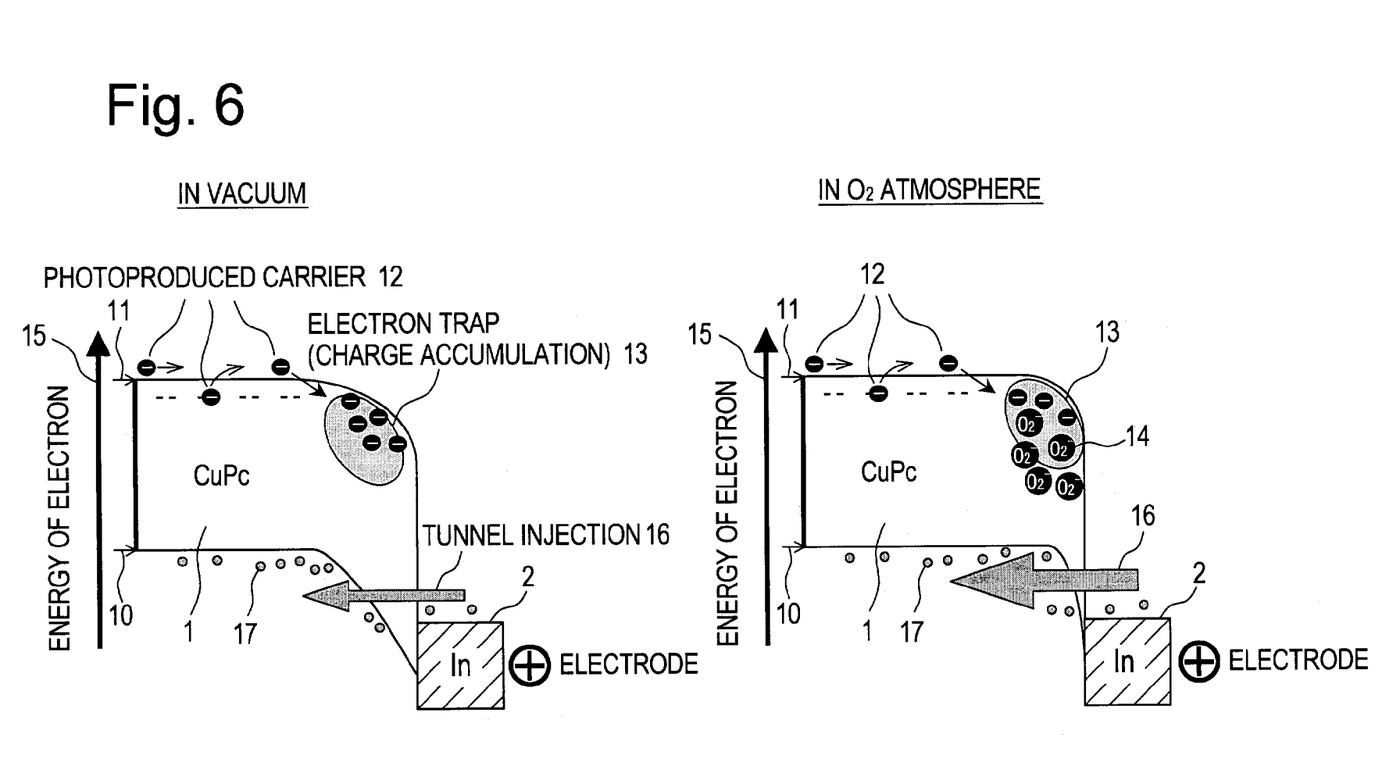
FIG. 6 shows energy diagrams at CuPc/In, namely an organic/metallic interface when the photocurrent multiplication phenomenon occurs in the same embodiment in vacuum for the left view and in oxygen atmosphere for the right view.

FIG. 6 shows energy diagrams at the organic/metallic interface, concretely at CuPc/In interface when the photocurrent multiplication phenomenon is occurring. The left view is an energy diagram in vacuum evacuated with a rotary pump and the right view is an energy diagram when oxygen is introduced. As the organic semiconductor, when the p-type CuPc is used, the photocurrent multiplication phenomenon occurs at the interface with the metallic electrode that is positively biased. The reference numeral 1 denotes CuPc, the reference numeral 2 denotes an In electrode to which a voltage is positively applied, the reference numeral 10 denotes a valence band, the reference numeral 11 denotes a conduction band, the reference numeral 12 denotes photoproduced electrons, the reference numeral 13 denotes electrons accumulated in the electron trap at the organic/metallic interface, the reference numeral 14 denotes electrons ($O_2^-$) that are trapped to oxygen molecules ($O_2$) adsorbed on the surface of the organic semiconductor, the reference numeral 15 denotes an energy of electron, the reference numeral 16 denotes tunnel injection of holes from the metallic electrode to the valence band, and the reference numeral 17 denotes holes that have been tunnel injected.

First, the photocurrent multiplication phenomenon at the CuPc/In interface in vacuum is activated in the following manner the electrons 12 that have been photoproduced in the CuPc are trapped and accumulated in the trap 13 in the vicinity of the In electrode 2 (this trap is considered as a spatial stop (structural trap) coming from the structural incompleteness existing at the organic/metallic interface); a high electric field is intensively applied; and finally the holes 17 are tunnel injected in the manner as denoted by the reference numeral 16 (photoinduced hole injection mechanism). That is, the photon needs to supply only the electrons 12 that are trapped at the interface, and once the tunnel injection is initiated, a large quantity of holes are injected into the device, with the result that the photocurrent multiplication phenomenon will occur by which more than 100 carries with respect to one photon flow through the device.

Next, as the oxygen is introduced, oxygen molecules are adsorbed on the CuPc surface. Since the adsorbed oxygen captures an electron to become the $O_2^-$ion 14, it seems to function as a trap of electron. That is, it can be explained that in the oxygen atmosphere, as a result of increase in the number of trap electrons, the electric field further concentrates to the interface and the number of holes to be tunnel-injected dramatically increases, so that the photocurrent amount due to multiplication significantly increases, or in other words, the photocurrent quantum yield (multiplication factor) increases.

Figure 7:
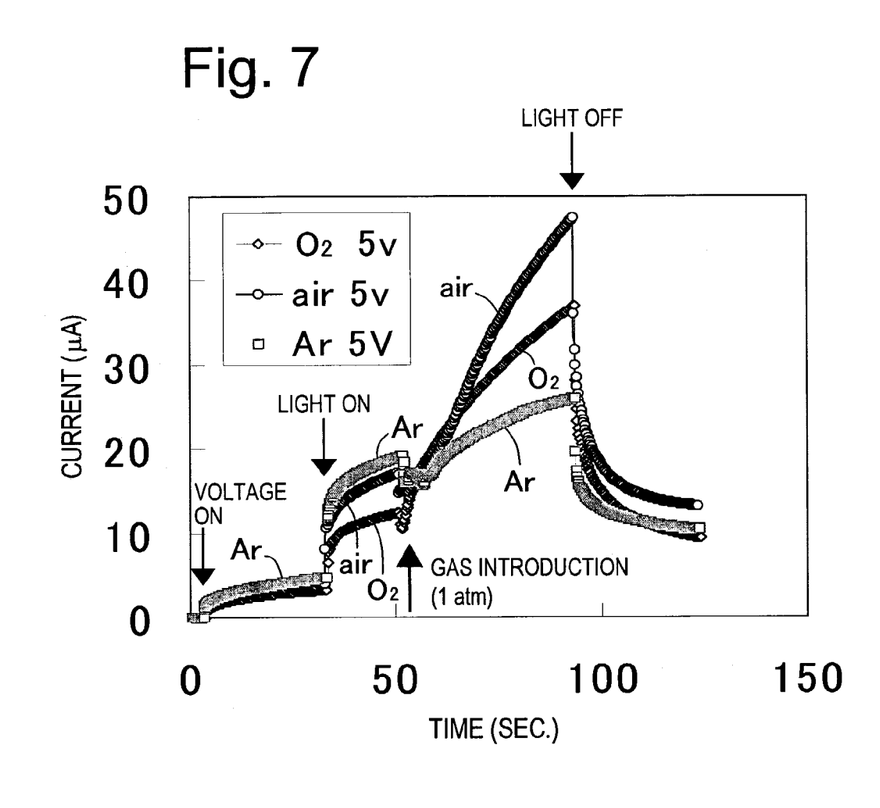
FIG. 7 is a graph showing responses to gas introduction of Ar, $O_2$ and Air in the same embodiment.

FIG. 7 shows responses to the Ar, $O_2$ and Air gases at the time of applying a voltage of 5V on the cell of FIG. 1. First, light irradiation is conducted in vacuum evacuated with a rotary pump, and then 1 atmospheric pressure of each gas is introduced.

As for the inert Ar gas, no change is observed (though the reason why the current once decreases immediately after introduction of gas is unknown, the current level recovers to the initial level thereafter).

When the pure oxygen is introduced, the current increases as described above.

When the air is introduced, the largest increase is observed. Although the oxygen concentration of this case is lower than that of when the pure oxygen is introduced because the air contains 20% of oxygen, the larger increase is observed due to the influence of the water vapor included in the air. This means that also the adsorbed water traps electrons likewise the oxygen and increases the injection current due to the multiplication, and that sensing of humidity is possible. This result suggests that the present device has sensitivity to various kinds of gases. It is to be noted, however, for the gas which, in contrast to the oxygen, traps holes and is easily oxidized, the multiplied photocurrent may sometimes decrease.

As described above, since the injection current detected in the present invention is the current that is multiplied by photocurrent multiplication, by the adsorbed gas molecules it is possible to obtain significant current change in the milli ampere order per 1 cm$^2$ in the injection current In principle, a current change of a larger number of electrons than the number of adsorbed gas molecules may occur. This means that the ratio between the number of carries having flown in the device and the number of gas molecules, namely, a value which can be considered as a quantum yield of number of electrons of current induced by adsorbed gas with respect to the number of adsorbed gas molecules (multiplication factor with respect to number of gas molecules), which is similar to the photocurrent quantum yield with respect to photon (multiplication factor) can be defined. This means multiplication sensing for gas molecules. In the conventional device that uses a change in resistance of organic semiconductor, since one gas molecule causes change of only one electron at most, such multiplication sensing cannot be realized in principle. In other words, since the multiplied photocurrent is observed while multiplying the trapped charges to several thousands of times, adsorbed molecules functioning as traps can be detected with high sensitivity.

Furthermore, since the adsorbed gas can be sensed insofar as it is adsorbed to the surface of the organic thin film, and the diffusion of gas into the bulk is not a rate-determining factor, a possibility of improving the response speed for the gas can be expected.

When a greater voltage is applied, it is predicted that the mechanism similar to that shown in FIG. 6 is activated by electrons that are injected to the conduction band during the dark period from the electrode of minus side, and a large amount of holes are tunnel-injected. Since also such a multiplied current during the dark period seems to be influenced by the adsorbed oxygen, it is considered in principle that in the high voltage operation of the present device, the gas sensing can be achieved by measuring a change in dark current in the absence of light irradiation. In this case, the electrode metal of minus side where multiplication does not occur is preferably a metal having a small work function from which electrons can be easily injected.

It is also possible to use metal free phthalocyanine other than copper phthalocyanine or phthalocyanine pigments containing other metals in the center. Also a p-type organic semiconductor can achieve sensing of oxygen in the similar mechanism. Although metals other than In may be used, it is preferred to use a metal having a small work function since the photocurrent multiplication phenomenon occurs at the interface where the Schottky junction is formed.

SECOND EMBODIMENT

Figure 8:
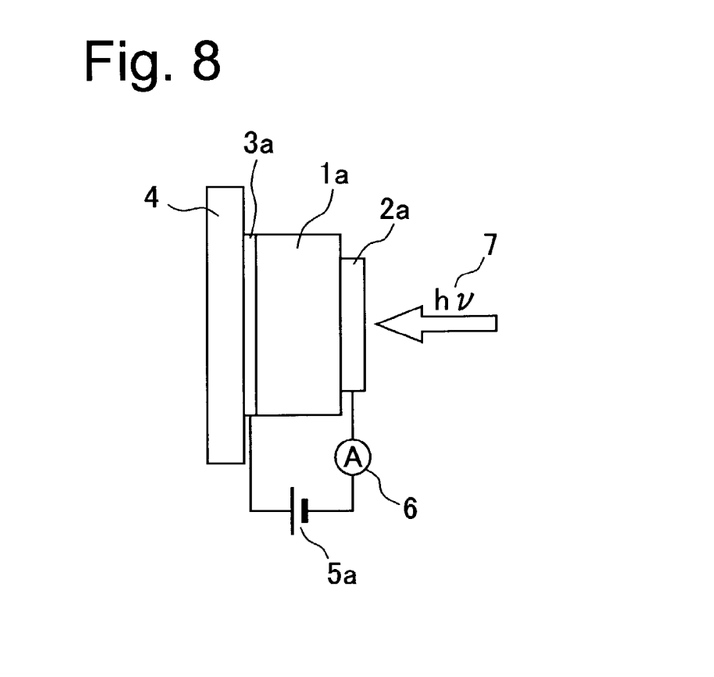
FIG. 8 is a section view showing a structure of another embodiment of a photocurrent multiplication gas sensor device of the present invention.

As the second embodiment, FIG. 8 shows an example wherein an n-type organic semiconductor is used. As an organic semiconductor thin film 1a, a perylene pigment (Me-PTC: represented by the chemical formula in FIG. 2) evaporated film having a film thickness of about 500 nm or a naphthalene derivative (NTCDA: represented by the chemical formula in FIG. 2) evaporated film having a film thickness of about 500 nm, which exhibits n-type semiconductor property, is used. As a metallic electrode 2a on the side where a gas to be sensed comes into contact and light is irradiated, an Au evaporated film having a film thickness of about 20 nm is used, and as the other metallic electrode 3a, an ITO (indium tin oxide) evaporated film having a film thickness of about 60 nm is used.

In the case of the n-type semiconductor, the photocurrent multiplication phenomenon occurs at the interface between the electrode to which the voltage is negatively applied and the organic semiconductor (as will be described later). For achieving this, a power source 5a is connected between the Au electrode 2a and the ITO electrode 3a so that the voltage is negatively applied to the Au electrode 2a with respect to the ITO electrode 3a. The reference numeral 6 denotes an ampere meter for monitoring current as is the embodiment in FIG. 1.

Figure 9:
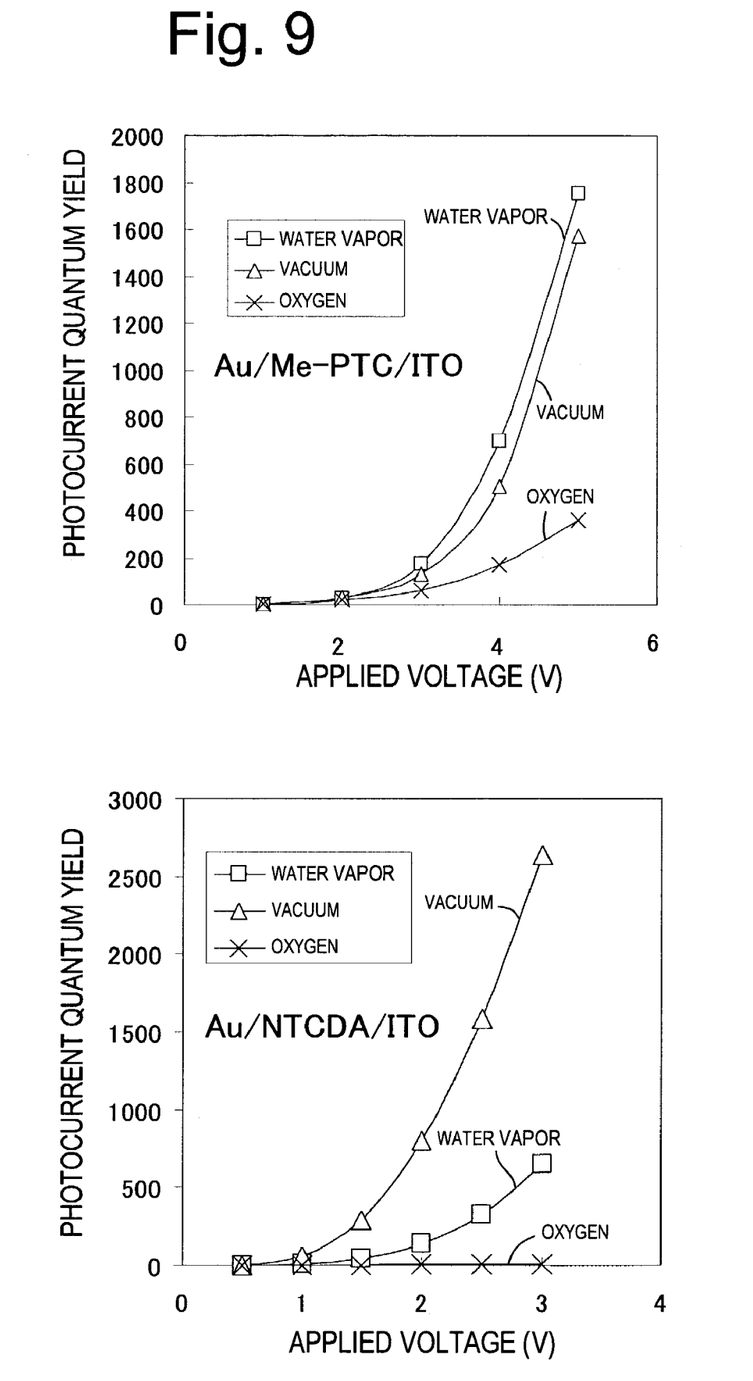
FIG. 9 is a graph showing dependence of photocurrent multiplication factor on applied voltage in vacuum and under introduction of 1 atmospheric pressure of pure oxygen in the same embodiment.

FIG. 9 shows dependence of photocurrent multiplication factor on applied voltage in vacuum evacuated by a rotary pump and under introduction of 1 atmospheric pressure of pure oxygen when the voltage is applied so that the Au electrode 2a is negative with respect to the ITO electrode 3a, in the present embodiment As for the multiplication phenomenon in the n-type organic semiconductor, the oxygen introduction provides a completely opposite effect to the p-type organic semiconductor. That is, in both of the Me-PTC and NTCDA, the multiplied photocurrent is significantly suppressed due to the introduction of oxygen.

Figure 10:
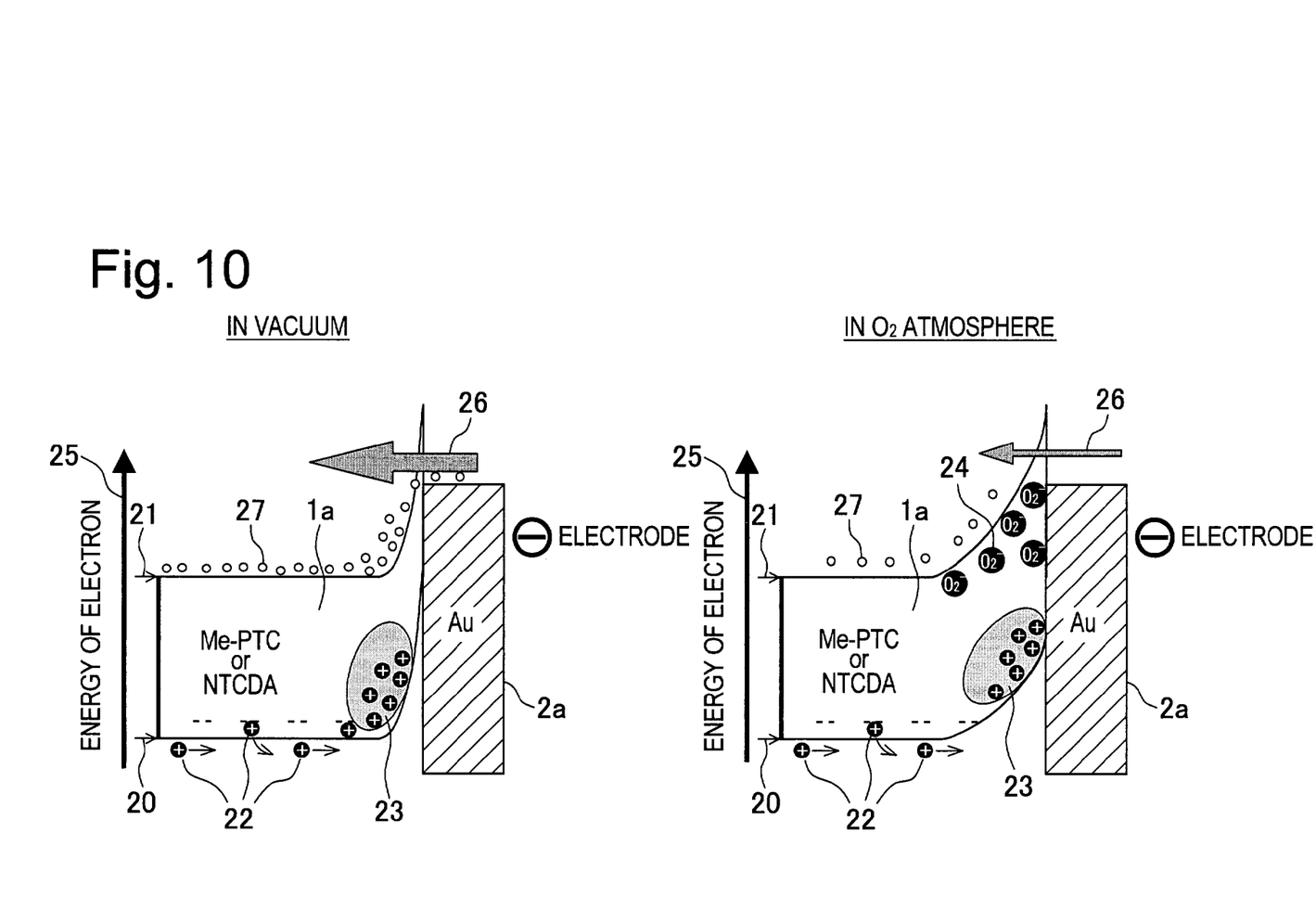
FIG. 10 shows energy diagrams at the Me-PTC interface or at the NTCD/Au interface when photocurrent multiplication occurs in the same embodiment in vacuum for the left view and in oxygen atmosphere for the right view.

FIG. 10 shows energy diagrams at Me-PTC or NTCDA/Au, that is, at the organic/metallic interface when the photocurrent multiplication phenomenon is occurring. The left view is an energy diagram in vacuum evacuated with a rotary pump and the right view is an energy diagram when oxygen is introduced. In the Me-PTC and NTCDA which are n-type semiconductors, the photocurrent multiplication phenomenon occurs at the interface with the metallic electrode that is negatively biased. The reference numeral 1 a denotes Me-PTC or NTCDA, the reference numeral 2a denotes an Au electrode which is negatively voltage-applied, the reference numeral 20 denotes a valence band, the reference numeral 21 denotes a conduction band, the reference numeral 22 denotes photoproduced holes, the reference numeral 23 denotes holes accumulated in the hole trap at the organic/metallic interface, the reference numeral 24 denotes electrons ($O_2^-$) that are trapped to oxygen molecules ($O_2$) adsorbed on the surface of the organic semiconductor surface, the reference numeral 25 denotes an energy of electron, the reference numeral 26 denotes tunnel injection of electrons from the metallic electrode to the conduction band, and the reference numeral 27 denotes electrons that have been tunnel injected.

It is known that in the case of n-type semiconductors, the multiplication phenomenon occurs in an inverted manner to the case of p-type semiconductors. That is, at the time of multiplication, part of the holes 22 that are photoproduced are trapped and accumulated in the traps in the vicinity of the negatively biased metallic electrode 2a. As a result of this, high electric field is intensively exerted to the interface between the organic thin film 1a and the metallic electrode 2a and finally a large amount of electrons are tunnel injected from the metallic electrode 2a to cause the multiplication (photoinduced electron injecting mechanism).

In this case, it is so considered that as the oxygen is adsorbed to the surface of the organic semiconductor 1a and traps the electrons to become a minus ion, an effective plus charge density at the organic/metallic interface reduces, and whereby the multiplication is suppressed. In this case, gas molecules that are likely to trap plus charges which are easily oxidized may possibly increase the multiplication factor.

FIG. 9 also shows the effect of water vapor (saturated vapor pressure under the condition where oxygen is absent after evacuation). Comparing the vacuum condition and the water vapor atmosphere condition, in the case of the NTCDA (lower view), it can be seen that adsorption of water suppresses the multiplication factor in the same way as oxygen. In the case of the Me-PTC (upper view), however, it acts to increase the multiplication factor though the action is small. It can be considered that a water molecule is not a trap that acts on only one of a hole or an electron. Since this element has the sensitivity to the water vapor, the present device also presents a possibility of use as a humidity sensor.

Also in this case, likewise the first embodiment, when a greater voltage is applied, it is predicted that the mechanism similar to that shown in FIG. 10 is activated by holes that are injected to the valence band during the dark period from the electrode of plus side, and a large amount of electrons are tunnel-injected. Since such a multiplication current during the dark period also seems to be influenced by the adsorbed oxygen, it is considered in principle that in the high voltage operation of the present device, the gas sensing can be achieved by measuring change in dark current in the absence of light irradiation. In this case, the electrode metal of plus side where multiplication does not occur is preferably a metal having a large work function from which holes can be easily injected.

INDUSTRIAL APPLICABILITY

The photocurrent multiplication gas sensor according to the present invention provides high sensitivity and high response speed since it senses gas by a change in injection current due to the photocurrent multiplication or dark current multiplication at the organic/metallic interface. Therefore, it can be used for environment monitoring or as a gas sensor for sensing oxygen, moisture and the like contained in a gas to be sensed in an apparatus for measuring exhaust gas from industrial plants or automobiles.

The invention claimed is:

1. A gas sensing method for sensing a gas to be sensed using a sandwich cell formed by sandwiching a photoconductive organic semiconductor layer between two metallic electrodes, the sandwich cell exhibiting a photocurrent multiplication phenomenon that a photocurrent occurring in the photoconductive organic semiconductor layer in response to light irradiation under application of a voltage by the electrodes is multiplied, the method comprising the steps of:
   (A) a step of irradiating the organic semiconductor layer with light in the condition that a voltage is applied on the organic semiconductor layer by the electrodes, thereby causing a multiplied photocurrent to generate at an organic/metallic interface, the voltage having such a magnitude that allows a photocurrent to flow between the electrodes in a quantum yield of not less than 1 when the organic semiconductor layer is irradiated with light;
   (B) a step of bringing the gas to be sensed into contact with the organic/metallic interface where photocurrent multiplication is occurring, in the condition of (A); and
   (C) a step of measuring a photocurrent flowing in the organic semiconductor layer to sense gas on the basis of a change in photocurrent associated with the contact of the gas to be sensed.

2. A gas sensing method for sensing a gas to be sensed using a sandwich cell formed by sandwiching an organic semiconductor layer between two metallic electrodes, the sandwich cell exhibiting a dark current multiplication phenomenon that a dark current occurring in the organic semiconductor layer under application of a voltage by the electrodes is multiplied, the method comprising the steps of:
   (A) a step of applying a voltage to the organic semiconductor layer by the electrodes to cause occurrence of a multiplied dark current at an organic/metallic interface, the voltage having such a magnitude that allows a dark current to flow between the electrodes in response to electrons or holes injected into the organic semiconductor layer in a quantum yield of not less than 1 with respect to the amount of injection;
   (B) a step of bringing the gas to be sensed into contact with the organic/metallic interface where multiplication of dark current is occurring, in the condition of (A); and
   (C) a step of measuring a dark current flowing in the organic semiconductor layer to sense gas on the basis of a change in dark current associated with the contact of the gas to be sensed.

3. A photocurrent multiplication gas sensor comprising:
   a sandwich cell formed by sandwiching a photoconductive organic semiconductor layer between two metallic electrodes, the sandwich cell exhibiting a photocurrent multiplication phenomenon that a photocurrent occurring in the photoconductive organic semiconductor layer in response to light irradiation under application of a voltage by the electrodes is multiplied;
   a power supply for applying a voltage to the organic semiconductor layer by the electrodes, the voltage having such a magnitude that allows a photocurrent to flow between the electrodes in a quantum yield of not less than 1 when the organic semiconductor layer is irradiated with light;
   an optical system for irradiating the organic semiconductor layer with light;
   an opening for bringing a gas to be sensed into contact with an organic/metallic interface where photocurrent multiplication occurs due to voltage application by the power supply and light irradiation by the optical system; and
   a current measuring circuit for measuring a photocurrent flowing in the organic semiconductor layer, thereby sensing a gas on the basis of a change in photocurrent associated with the contact of the gas to be sensed.

4. The gas sensor according to claim 3, wherein the organic semiconductor layer is a p-type organic semiconductor layer, the power supply applies a voltage so as to bias the metallic electrode of the organic/metallic interface where the photocurrent multiplication should occur to the plus voltage side, and the gas sensor is intended to sense oxygen or moisture based on an increase in the photocurrent.

5. The gas sensor according to claim 4, wherein the p-type organic semiconductor layer is formed of a phthalocyanine pigment.

6. The gas sensor according to claim 4 or 5, wherein the metallic electrode of the organic/metallic interface where the photocurrent multiplication should occur is formed of a metal having a small work function.

7. The gas sensor according to claim 6, wherein the metallic electrode of the organic/metallic interface where the photocurrent multiplication should occur is formed of indium.

8. The gas sensor according to claim 3, wherein the organic semiconductor layer is an n-type organic semiconductor layer, the power supply applies a voltage so as to bias the metallic electrode of the organic/metallic interface where the photocurrent multiplication should occur to the minus voltage side, and the gas sensor is intended to sense oxygen based on a decrease in the photocurrent.

9. The gas sensor according to claim 8, wherein the organic semiconductor layer is formed of a perylene pigment or a naphthalene derivative.

10. The gas sensor according to claim 3, wherein
the organic semiconductor layer is formed of a naphthalene derivative which is an n-type organic semiconductor layer,
the power supply applies a voltage so that the metallic electrode of the organic/metallic interface where the photocurrent multiplication should occur is biased to the minus voltage side, and
the gas sensor is intended to sense moisture based on a decrease in the photocurrent.

11. The gas sensor according to claim 8, 9 or 10, wherein the metallic electrode of the organic/metallic interface where the photocurrent multiplication should occur is formed of a metal having a large work function.

12. The gas sensor according to claim 3, wherein the voltage applied by the power supply is set so as to cause a current change of larger number of electrons than the number of adsorbed gas molecules.

13. A current multiplication gas sensor comprising:
a sandwich cell fanned by sandwiching an organic semiconductor layer between two metallic electrodes, the sandwich cell exhibiting a dark current multiplication phenomenon that a dark current occurring in the organic semiconductor layer under application of a voltage by the electrodes is multiplied;
a power supply for applying a voltage to the organic semiconductor layer by the electrodes, the voltage having such a magnitude that allows a dark current to flow between the electrodes in response to electrons or holes injected into the organic semiconductor layer in a quantum yield of not less than 1 with respect to the amount of injection;
an opening for bringing a gas to be sensed into contact with an organic/metallic interface where current multiplication occurs due to voltage application by the power supply; and
a current measuring circuit for measuring a dark current flowing in the organic semiconductor layer, thereby sensing a gas on the basis of a change in dark current associated with the contact of the gas to be sensed.

14. The gas sensor according to claim 3, wherein the organic semiconductor layer is a evaporated film.

15. The gas sensor according to claim 3 or 13, wherein the organic semiconductor layer is a resin dispersed organic semiconductor film formed by dispersing an organic semiconductor in a resin.

* * * * *